(12) United States Patent
Almli et al.

(10) Patent No.: US 6,723,042 B2
(45) Date of Patent: Apr. 20, 2004

(54) PENILE PUMP WITH SIDE RELEASE MECHANISM

(75) Inventors: John G. Almli, Chaska, MN (US); Charles C. Kuyava, Eden Prairie, MN (US); Randy L. Morningstar, Brooklyn Park, MN (US); Kevin R. Watts, Plymouth, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 10/006,335

(22) Filed: Dec. 3, 2001

(65) Prior Publication Data

US 2002/0082709 A1 Jun. 27, 2002

Related U.S. Application Data

(63) Continuation-in-part of application No. 09/749,075, filed on Dec. 27, 2000, now abandoned.
(60) Provisional application No. 60/295,326, filed on Jun. 1, 2001.

(51) Int. Cl.$^7$ .................................................. A61F 2/02
(52) U.S. Cl. ......................................................... 600/40
(58) Field of Search ........................ 623/11; 600/38–41, 600/29–32; 128/DIG. 25, 843

(56) References Cited

U.S. PATENT DOCUMENTS

| | | |
|---|---|---|
| 988,120 A | 3/1911 | Lott |
| 1,863,057 A | 6/1932 | Innes |
| 3,312,215 A | 4/1967 | Silber |
| 3,344,791 A | 10/1967 | Foderick |
| 3,397,699 A | 8/1968 | Kohl |
| 3,503,400 A | 3/1970 | Osthagen et al. |
| 3,642,004 A | 2/1972 | Osthagen et al. |
| 3,731,670 A | 5/1973 | Loe |
| 3,797,478 A | 3/1974 | Walsh et al. |
| 3,812,841 A | 5/1974 | Isaacson |
| 3,954,102 A | 5/1976 | Buuck |
| 4,222,377 A | 9/1980 | Burton |
| 4,256,093 A * | 3/1981 | Helms et al. .................. 600/31 |
| 4,267,829 A | 5/1981 | Burton et al. |
| 4,344,434 A | 8/1982 | Robertson |
| 4,383,525 A | 5/1983 | Scott et al. |
| 4,407,278 A | 10/1983 | Burton et al. |
| 4,412,530 A | 11/1983 | Burton |
| 4,437,457 A * | 3/1984 | Trick et al. .................... 600/31 |
| 4,453,536 A | 6/1984 | Abild |
| 4,489,732 A | 12/1984 | Hasson |
| 4,537,183 A | 8/1985 | Fogarty |
| 4,553,959 A | 11/1985 | Hickey et al. |
| 4,558,693 A * | 12/1985 | Lash et al. ..................... 600/40 |
| 4,566,446 A | 1/1986 | Fogarty |
| 4,571,241 A | 2/1986 | Christopher |
| 4,587,954 A * | 5/1986 | Haber .......................... 600/31 |
| 4,590,927 A | 5/1986 | Porter et al. |
| 4,632,435 A | 12/1986 | Polyak |
| 4,671,261 A | 6/1987 | Fischell |
| 4,682,583 A | 7/1987 | Burton et al. |
| 4,710,169 A | 12/1987 | Christopher |
| 4,718,410 A | 1/1988 | Hakky |

(List continued on next page.)

Primary Examiner—Samuel G. Gilbert
(74) Attorney, Agent, or Firm—Jeffrey J. Hohenshell

(57) ABSTRACT

A pump and valve assembly for an implantable prosthesis is provided with an internal actuating bar positioned such that when any portion of the housing is compressed, the check valves within are opened allowing for deflation of the cylinders. The pump and valve assembly also includes a textured surface over a portion of the housing to allow for quick identification of the component, as well as to make it easier for the patient to grasp it. The valve assembly further comprising an actuating bar which has ribs to enhance the spring force applied to a flow valve, a support structure to support and appropriately position the actuating bar, and a check valve made of metal with a segment covered with a plastic material.

11 Claims, 10 Drawing Sheets

U.S. PATENT DOCUMENTS

| | | | |
|---|---|---|---|
| 4,773,403 A | * 9/1988 | Daly | 600/40 |
| 4,782,826 A | 11/1988 | Fogarty | |
| 4,829,990 A | * 5/1989 | Thuroff et al. | 600/40 |
| 4,850,963 A | 7/1989 | Sparks et al. | |
| 4,881,530 A | * 11/1989 | Trick | 600/40 |
| 4,932,938 A | 6/1990 | Goldberg et al. | |
| 4,944,732 A | 7/1990 | Russo | |
| 4,958,630 A | 9/1990 | Rosenbluth et al. | |
| 4,968,294 A | 11/1990 | Salama | |
| 5,030,199 A | 7/1991 | Barwick et al. | |
| 5,034,009 A | 7/1991 | Mouchel | |
| 5,041,092 A | 8/1991 | Barwick | |
| 5,048,510 A | 9/1991 | Hauschild et al. | |
| 5,048,511 A | * 9/1991 | Rosenbluth et al. | 600/40 |
| 5,062,417 A | 11/1991 | Cowen | |
| 5,063,914 A | 11/1991 | Cowen | |
| 5,074,849 A | 12/1991 | Sachse | |
| 5,085,650 A | 2/1992 | Giglio | |
| 5,088,980 A | 2/1992 | Leighton | |
| 5,090,424 A | 2/1992 | Simon et al. | |
| 5,112,295 A | 5/1992 | Zinner et al. | |
| 5,114,398 A | 5/1992 | Trick et al. | |
| 5,131,906 A | 7/1992 | Chen | |
| 5,141,509 A | 8/1992 | Burton et al. | |
| 5,167,611 A | 12/1992 | Cowan | |
| 5,171,272 A | 12/1992 | Levius | |
| 5,186,180 A | 2/1993 | Bellas | |
| 5,250,020 A | 10/1993 | Bley | |
| 5,344,388 A | 9/1994 | Maxwell et al. | |
| 5,518,499 A | * 5/1996 | Agar | 600/40 |
| 5,704,895 A | 1/1998 | Scott et al. | |
| 5,851,176 A | 12/1998 | Willard | |
| 5,893,826 A | * 4/1999 | Salama | 600/31 |
| 5,895,424 A | 4/1999 | Steele, Sr. et al. | |
| 6,171,233 B1 | 1/2001 | Willard | |

\* cited by examiner

PENILE PUMP WITH SIDE RELEASE MECHANISM

CROSS REFERENCE TO RELATED APPLICATIONS

This application is a continuation-in-part of related patent application Ser. No. 09/749,075 now abandoned, entitled "PENILE PUMP WITH SIDE RELEASE MECHANISM" which was filed on Dec. 27, 2000, and claims the priority of provisional application Ser. No. 60/295,326 entitled "PENILE PUMP IMPROVEMENTS" which was filed Jun. 1, 2001 (the entire contents of each of which are herein incorporated by reference).

BACKGROUND

This invention generally relates to a pump and valve assembly for inflating a prosthesis. More particularly, the invention relates to pressure-based mechanisms that inhibit spontaneous inflation of the prosthesis, including stiffening and support mechanisms that also improve the function of the valve.

One common treatment for male erectile dysfunction is the implantation of a penile prosthesis. Such a prosthesis typically includes a pair of inflatable cylinders, which are fluidly connected to a reservoir (typically liquid filled) via a pump and valve assembly. The two cylinders are normally implanted into the corpus cavernosae of the patient and the reservoir is typically implanted into the patient's abdomen. The pump assembly is implanted in the scrotum.

During use, the patient actuates the pump and fluid is transferred from the reservoir through the pump and into the cylinders. This results in the inflation of the cylinders and thereby produces the desired penis rigidity for a normal erection. Then, when the patient desires to deflate the cylinders, a valve assembly within the pump is actuated in a manner such that the fluid in the cylinders is released back into the reservoir. This deflation then returns the penis to a flaccid state.

Presently, the pump and valve assembly used in such implantable prostheses share certain similar characteristics. For example, they include fluid pathways allowing the flow of fluid to and from the reservoir, as well as to and from the cylinders. This fluid flow is controlled by one or more check valves positioned in the fluid pathways within the housing of the assembly.

A compressible pump bulb is also attached to the housing and is in fluid communication with the various fluid pathways therethrough. In order to inflate the cylinders, the compressible pump bulb is actuated by the patient, thereby urging fluid past the check valves into the cylinders. In order to deflate the cylinders, the valve housing is grasped and squeezed (through the patient's tissue), causing the various check valves to unseat and allow fluid to flow back to the reservoir.

Since the pump and valve assembly is positioned within the patient's scrotum, the various components of the assembly must be small. As a result, manipulation of the pump and valve assembly is sometimes difficult. For example, patients requiring the use of penile prosthesis discussed herein are oftentimes elderly and have a reduced dexterity as a result of aging. Thus, in some instances, even locating the device within the tissue can be a challenge, let alone identifying the correct portion of the assembly to actuate. More specifically, with some patients, it may be difficult to determine whether the housing portion of the assembly that leads to release or deflation of the cylinders is being grasped or whether the bulb portion which would be used to inflate the cylinders is being grasped.

Notably, the length of the valve assembly is determined (at least in one direction) by the size of the various check valves and the distance such valves must move in order to open and close the various fluid passageways. As a result, such a pump and valve assembly typically is longer in a direction parallel with the check valves. Moreover, in order to release the check valves in an assembly configured in this manner, the patient must grasp the narrower, shorter side walls of the assembly and compress them together. Since such a configuration can present challenges insofar as the spring tension of the check valves at the time of desired deflation is typically at a maximum while the surface area of the assembly which must be compressed in order to cause such deflation is at a minimum. This condition can lead to a situation where the patient has difficulty actually compressing the assembly, or in extreme circumstances, actually loses grip of the assembly during such attempts at deflation.

Although the existing devices function with extreme efficiency and reliability, for some patients it appears there is a desire for a pump and valve assembly in an implantable prosthesis that improves operative manipulation of the assembly. One such prosthesis pump is disclosed in co-pending U.S. patent application Ser. No. 09/749,075, entitled "Penile Pump With Side Release Mechanism," which is assigned to the Assignee of the present invention and is incorporated herein by reference. However, the operational efficiency of the prosthesis pump could be further improved by optimizing the function of the check valves.

Metal on metal contact can cause undesired wear of components over time. This can affect the performance of any product. In the pump and valve assembly, the check valve and spring engage one another at an end of the check valve to inhibit movement. Typically, at least a portion of the check valve and spring are made of a metal material such as stainless steel. The repeated application of a spring force by the spring onto the end of the check valve tends to wear or degrade the contact portions of the check valve and spring. This metal on metal contact over time negatively impacts the performance of the valve assembly.

The orientation of the pump and valve assembly creates a condition where the spring applies a force in both the axial and sideways directions onto the check valve, during actuation of the prosthesis pump. The axial force acts to move the check valve poppet into the valve assembly, while the side force has the unintended consequence of pushing the check valve sideways causing the valve to tip sideways. When the check valve is pushed sideways into the valve housing, the valve housing deforms which causes the check valve to be misaligned. This results in the check valve being restrained from moving axially into the valve housing to reach its open position.

Finally, the repeated exertion of axial and side forces of the spring on the end of the check valve tends to cause a reduction in the stiffness of the of the spring. Specifically, the spring is a thin elongate member having a bent portion. As a patient grasps the narrower, shorter side walls of the assembly and compresses them together, the spring flexes inwardly to force, via axial and side forces, the check valve to move to an open position. When the patient releases the side walls of the assembly the spring returns to its original position, permitting the check valve to return to a closed position. The repeated flexing of the spring may cause a reduction in stiffness of the spring, particularly at the bend.

This reduction in stiffness may lead to the spring deflecting during actuation in an unintended manner, which can permanently deform the spring. Permanent deformation of the spring has the undesired effect of inhibiting the full axial travel of the check valve between the open and closed positions.

There exists a need to provide a prosthetic penile implant that reduces the wear of the contact point of the check valve and the spring. There is a desire to improve the function of the valve assembly by prevention of deformation of the valve housing and misalignment of the check valve. There is a need to provide a barrier to sideways movement of the check valve when moving between the open and closed positions. Additionally, there is a desire to increase the strength and stiffness of the spring to prevent the spring from deflecting during actuation and prevent permanent deformation of the spring.

BRIEF SUMMARY OF THE INVENTION

The present invention provides various features which taken alone or in combination with one another provide for an improved pump and valve assembly for an implantable prosthesis. The present pump and valve assembly includes a pump bulb that must be differentiated from the valve housing when inflation of the cylinders is desired. The pump bulb itself has dimensions that are somewhat different than the remainder of the housing. However, to supplement differentiation between the bulb and the valve housing, the valve housing is provided with a textured surface so that even through tissue the patient is able to readily discern which area comprises the pump bulb and which area comprises the valve housing. This is important in that the pump bulb is compressed for inflation while the valve housing is compressed for deflation.

The pump assembly of the present invention is also configured such that it has a length longer than its width, with its internal check valves running parallel with the length. To release fluid from the inflated cylinders, the internal check valves are actuated so that they move in a direction parallel to the length, until they open. To achieve this action directly, the opposing sides of the width of the valve housing are compressed. This compression causes actuation of the internal check valves.

In addition, an actuating bar is positioned within the valve housing parallel with and extending along at least one of the sides of the length. An arm attached to the actuating bar extends along a portion of one of the sides of the width in close proximity to the tip of one of the check valves. Thus, the configuration of the actuating bar causes it to engage and open the check valve allowing fluid to flow from the cylinder to the reservoir. Furthermore, the patient can grasp the valve housing in virtually any orientation and when pressure is applied, the actuating bar will act either directly or indirectly to open the appropriate check valves. Thus, so long as the patient grasps any portion of the pump and valve assembly other than the pump bulb, compression will result in the desired opening of the check valves which will allow the cylinders to deflate.

Furthermore, since the patient can grasp the valve housing along the sides of the length, i.e., surfaces with larger surface area, less pressure need be applied to achieve the successful opening of the check valves. In other words, by increasing the surface area that is engaged by the patient's fingers and appropriately positioning the actuating bar, less force need be exerted by the patient to achieve the desired result.

The textured surface of the valve housing not only helps the patient identify the correct portion of the pump and valve assembly to actuate, it also serves to prevent slippage once the patient begins to compress the housing. Thus, what is achieved is an efficient and ergonomic pump and valve assembly for an implantable prosthesis. The pump and valve assembly can advantageously be formed from a minimal number of components. That is, all that need be molded are a valve block and a corresponding pump bulb which surrounds the valve block. The various check valves can be inserted into the valve block and then placed within the interior of the pump bulb, thus forming a completed assembly. This results in certain manufacturing efficiencies, thus reducing both cost and time of production.

To further improve the operational efficiency of the pump and valve assembly, the check valve is made of a metal material with a plastic member disposed over a segment of the metal material. The plastic segment of the check valve prevents undesired frictional metal on metal contact with the actuating bar, and prevents premature wearing of the contact point of the two components.

To further improve the life of the valve assembly, ribs, that extend across a bend, are added to the actuating bar. This modification increases the strength and stiffness of the spring and prevents the actuating arm from deflecting during actuation. In turn, full axial travel of the check valve is ensured. Increasing the strength of the bend also prevents permanent deformation of the spring when normal deflection occurs during actuation of the valve assembly. Another rib is disposed along the actuation face of the actuating bar to limit deformation of the actuation face during actuation of the valve assembly.

To improve the ease of deflation, a stiff poppet support wraps around the valve body and rests against a portion of the check valve. The poppet support has a shelf that provides smooth surface for a portion of the check valve to slide along. The poppet support contacts the check valve and prevents undesirable sideways movement of the check valve against the valve body. The positioning and configuration of the poppet support thus allows the check valve to easily move axially into the valve body to an open position. This results in improved operational efficiency of the check valve and an extended operating life.

DETAILED DESCRIPTION OF THE INVENTION

Figure 1:
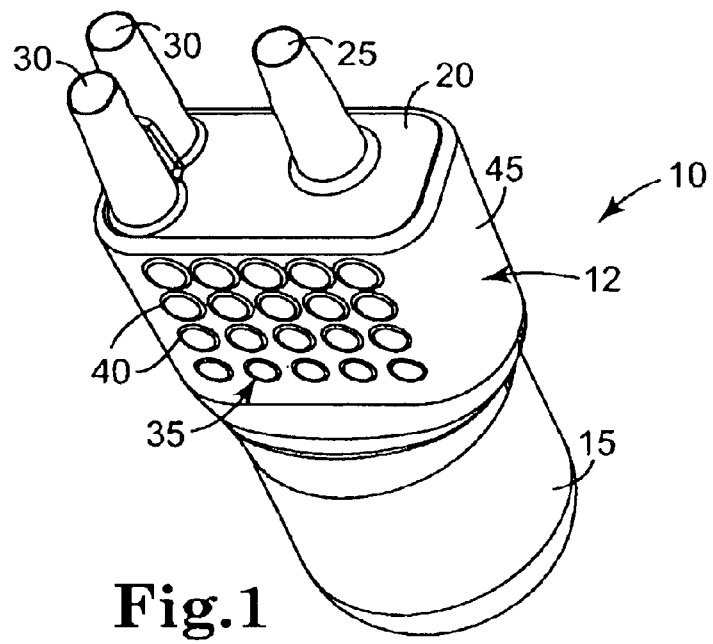
FIG. 1 is a perspective view of a pump and valve assembly according to the present invention.

Referring to FIG. 1, a pump and valve assembly is illustrated and generally referred to as 10. Pump and valve assembly 10 includes two different sections: valve housing 12 and pump bulb 15. Pump bulb 15 is a compressible member, defining a chamber more clearly shown in FIG. 2. Valve housing 12 is fluidly coupled to pump bulb 15 and contains the various other working components of pump and valve assembly 10. Pump and valve assembly 10 will be fluidly coupled to a reservoir and a pair of cylinders (not shown). This is accomplished through tubing connected to reservoir coupling 25 and cylinder couplings 30, which are integral with valve housing 12. Pump and valve assembly 10 is configured such that pump bulb 15 extends from one end of valve housing 12, while reservoir coupling 25 and cylinder couplings 30 extend from the other. Thus, when implanted in the patient, reservoir coupling 25 and cylinder couplings 30, and the fluid tubing they are coupled to, are oriented toward the patient's abdomen, while the pump bulb 15 is disposed in the opposite direction. Therefore, when pump bulb 15 is grasped by a patient, there is no interference from or contact with the tubing coupled to reservoir coupling 25 and cylinder couplings 30.

Valve housing 12 is illustrated as being generally rectangular, having a first major panel 35 that is longer than first minor panel 45. The length of first major panel 35 is determined by the distance required to incorporate the various check valves described below and allow their proper functioning. Likewise, first minor panel 45 need only be long enough to incorporate the width of these check valves and once again allow their proper functioning. Of course, some consideration can be given to the optimal diameter of the fluid tubing and couplings connecting pump and valve assembly 10 to the reservoir and cylinders. Though shown as being generally rectangular, valve housing 12 can take on any configuration (and dimension) so long as the check valves contained therein operate correctly. The illustrated configuration generally minimizes the volume required for valve housing 12 to operate effectively. Thus, the net result is that first major panel 35 is generally longer than first minor panel 45.

Figure 2:
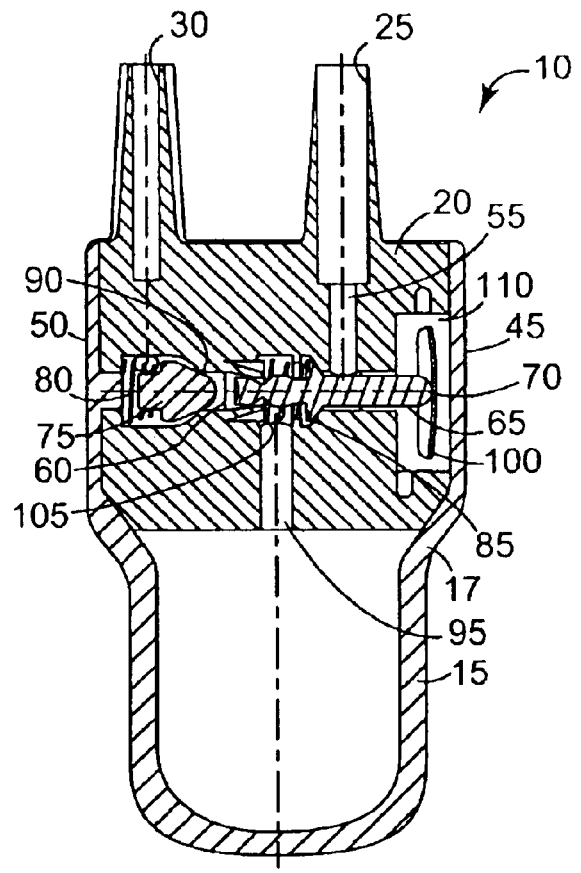
FIG. 2 is a front sectional view of the pump and valve assembly illustrated in FIG. 1.

Referring to FIGS. 1 and 2, the internal configuration of pump and valve assembly 10 will be described. Two separate molded components are utilized to form pump and valve assembly 10. That is, valve block 20 is combined with shell 17 to form the completed unit. Pump bulb 15 and valve housing 12 are a single, integral unit referred to as shell 17 that substantially surrounds valve block 20. As illustrated, shell 17 includes valve housing 12 which surrounds valve block 20. Alternatively, shell 17 could be a smaller component that does not surround valve block 20, but is simply coupled to it. In either case, only two molded components need be provided to complete the device. These components can be formed from silicone or any other appropriate material.

The use of only two molded components to form pump and valve assembly 10 is advantageous. Previous devices generally have four or more molded components which must be individually put together. Only two components can be bonded in a single step. Bonding includes heating, using adhesive, or various other joining techniques. The two bonded components then take time to set up before the next component can be added. Thus, a four component device results in a fairly long manufacturing process having increased costs associated therewith.

With the present device, valve block 20 is molded and the various valve components are inserted into place. Shell 17 is then attached and bonded. Thus, only a single bonding or adhering step is required to complete the product. This greatly increases throughput, decreases costs, and decreases manufacturing time without sacrificing quality or durability.

Located within valve block 20 are a plurality of fluid passageways coupling reservoir coupling 25 and cylinder couplings 30 to pump bulb 15 through bulb passageway 95 via medial passageway 60. Disposed within medial passageway 60 are two spring-actuated poppets: a reservoir poppet 65 and a cylinder poppet 75, which respectively and selectively abut reservoir poppet valve seat 85 and cylinder poppet valve seat 90. Cylinder poppet 75 is an uncomplicated, ball-shaped or conical-shaped check valve. Reservoir poppet 65 is an elongated member having a somewhat more complicated shape. The configuration of reservoir poppet 65, along with the configuration of valve block 20 along medial passageway 60 is designed to allow the proper operation of the poppets while also preventing spontaneous inflation. The functionality and operability of this arrangement is discussed in co-pending applications Ser. No. 09/749,292, filed on Dec. 27, 2000, and entitled "Pressure Based Spontaneous Inflation Inhibitor," and Ser. No. 10/010,498, filed concurrently herewith, and entitled "Pressure Based Spontaneous Inflation Inhibitor With Penile Pump Improvements," the entire disclosures of which are herein incorporated by reference.

During a compression of pump bulb 15, fluid is forced from the internal chamber of pump bulb 15 through bulb passageway 95, causing cylinder poppet 75 to open and allow fluid to flow through cylinder couplings 30 into the respective cylinders. When pump bulb 15 is released, cylinder poppet 75 closes under spring pressure. The vacuum generated by pump bulb 15 causes reservoir poppet 65 to unseat itself and allow fluid to flow from the reservoir through reservoir coupling 25 so that fluid once again fills pump bulb 15. Repeated compressions are performed to entirely inflate the cylinders to the patient's satisfaction.

When it is desired to deflate the cylinders, the patient compresses valve housing 12 by squeezing first minor panel 45 towards second minor panel 50. As this occurs, the outer wall of valve housing 12 engages actuating bar arm 130 which engages reservoir poppet tip 70, causing reservoir poppet 65 to unseat itself as well as unseating cylinder poppet 75. Fluid is then able to flow from the cylinders to the reservoir through medial passageway 60. When satisfactorily deflated, the patient releases valve housing 12, allowing reservoir poppet 65 and cylinder poppet 75 to reseat themselves and prevent fluid flow.

To perform the above described deflation process, the patient may compress first minor panel 45 and second minor panel 50. In some patients, however, it may be difficult to achieve this compression because of the relatively small size of first and second minor panels 45 and 50. Likewise, it may be difficult for certain patients to grasp valve housing 12 in this manner since valve housing 12 may slip out of position between the patient's fingers. Thus, the present pump and valve assembly 10 provides an actuating bar 100 that allows the patient to grasp the first major panel 35 and second major panel 120 (as illustrated in FIGS. 3–5).

Figure 3:
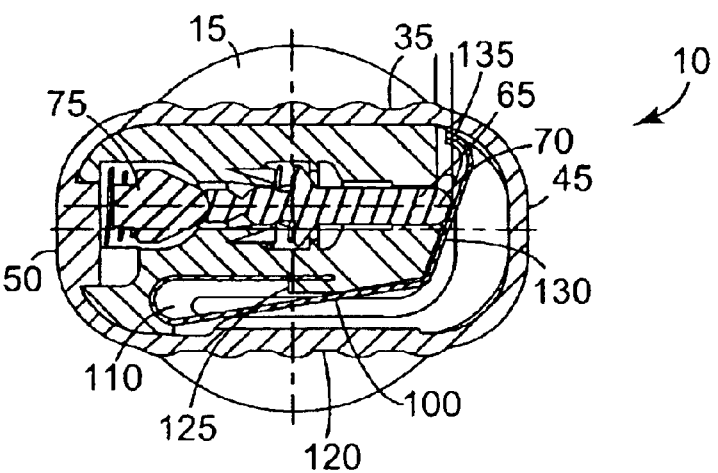
FIG. 3 is a top sectional view of the pump and valve assembly illustrated in FIG. 1, shown in a state where the cylinders are being deflated.

Referring to FIG. 3, the operation of actuating bar 100 is illustrated. Actuating bar 100 is disposed within valve block 20 by frictionally securing one end of actuating bar 100 into valve block interface 125 which securely holds it in place. Actuating bar 100 extends substantially along the length of major panel 120. Actuating bar arm 130 is integrally coupled with actuating bar 100 and generally extends substantially along the length of first minor panel 45. Actuating bar 100 is comprised of a suitable material, such as stainless steel or plastic. FIG. 3 illustrates a configuration of actuating bar 100 when a patient is compressing valve housing 12. The configuration illustrated in FIG. 4 is that of a deactivated state. In this state, the patient does not intend to inflate (nor deflate) the cylinders. The relationship between reservoir poppet 65 and valve block 20 in the area of medial passageway 60 is such that spontaneous inflation is prevented. FIG. 5 illustrates a pumping state. Reservoir poppet 65 is moved to the right (as illustrated) and tip 70 abuts arm 130. When pump bulb pressure is sufficient, cylinder poppet 75 will be unseated. FIG. 4 illustrates the position of actuating bar 100 in a deactivated state, that is, when the patient is not compressing valve housing 12.

Returning to FIG. 1, major panels 35 and 120 contain a textured surface 40, containing a plurality of raised sections. These raised sections make it easy for the patient to identify and distinguish valve housing 12 from pump bulb 15 and also allow the patient to grasp it better. Furthermore, because major panels 35 and 120 are relatively large in comparison to minor panels 45 and 50, it is easier for the patient to grasp and compress these major panels 35 and 120.

Figure 4:
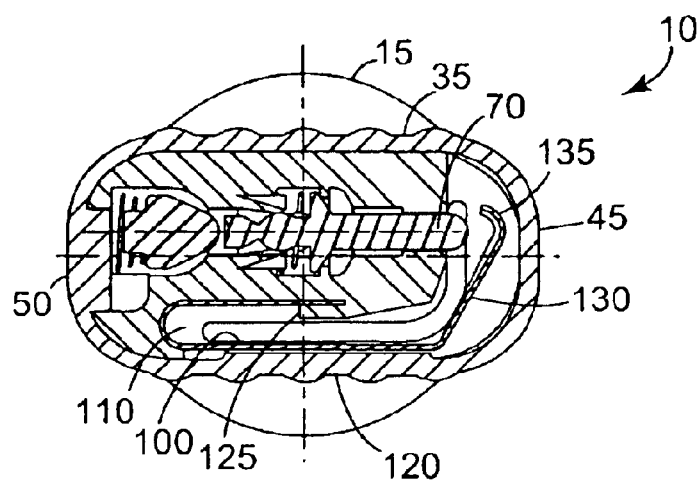
FIG. 4 is a top sectional view of the pump and valve assembly illustrated in FIG. 1, shown in a state where the check valves are in a deactivated position.
Figure 5:
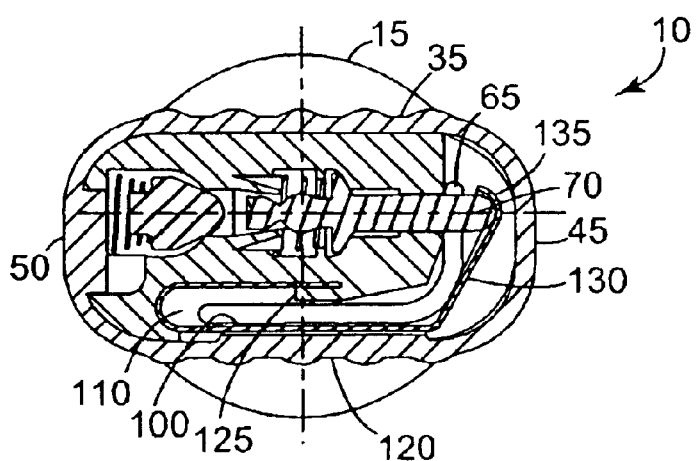
FIG. 5 is a top sectional view of the pump and valve assembly illustrated in FIG. 1, shown in a state where the check valves are in a pumping position.

Referring once again to FIG. 3, when major panels 35 and 120 are compressed towards one another, actuating bar 100 is deflected from the position illustrated in FIG. 4 to the position illustrated in FIG. 3. Thus, by engaging reservoir poppet tip 70, actuating bar arm 130 forces reservoir poppet 65 to move towards and open cylinder poppet 75. More specifically, actuating bar 100 is generally parallel with second major panel 120 in the deactivated stage. When engaged, actuating bar 100 is deflected towards first major panel 35. Because of the angle between actuating bar 100 and actuating bar arm 130, actuating bar arm 130 is caused to move towards reservoir poppet tip 70, as well as first major panel 35. Insofar as this movement is defined by the internal wall of valve housing 12, actuating bar arm 130 moves to the position illustrated in FIG. 3, engaging and opening reservoir poppet 65. Of course, this does not preclude the patient from grasping first minor panel 45 and second minor panel 50 and compressing them towards one another. If this is done, reservoir poppet 65 will likewise be effectively unseated. As such, it should be noted that the patient can grasp valve housing 12 in numerous orientations and a compression will effectively either directly engage reservoir poppet 65 or cause actuating bar 100, and more particularly actuating bar arm 130 to engage and open reservoir poppet 65. Thus, the patient need not maintain any particular orientation of valve housing 12 while deflating the cylinders. That is, any grip achieved on the valve housing 12 can be utilized to effectively open the poppets.

The configuration of major panels 35 and 120, including textured surface 40, will allow patients to easily identify the portion of valve housing 12 having a larger surface area and to grip it more effectively. When doing so, it may seem to the patient that less force need be applied in order to unseat reservoir poppet 65. That is, the spring tensions involved are constant for cylinder poppet 75 and reservoir poppet 65. However, because of the larger surface area of major panels 35 and 120, as compared to minor panels 45 and 50, the patient need apply less force in order to successfully actuate the device.

The configurations illustrated in FIGS. 4 and 5 differ only in that reservoir poppet 65 is in different positions with respect to valve block 20, depending upon whether the device is in a deactivated state as in FIG. 4 or in a pumping state as in FIG. 5. This is more a characteristic of the spontaneous inflation preventing mechanism as mentioned above, rather than being directly related to the operation of actuating bar 100. Of note, actuating bar arm 130 is configured to receive reservoir poppet tip 70 during the pumping stage as illustrated in FIG. 5. That is, during the compression of pump bulb 15 fluid pressure will force reservoir poppet 65 to its right most position as illustrated in FIG. 5. Because of the configuration of actuating bar arm 130 in its unbiased position, it will not interfere with this operation.

Figure 6:
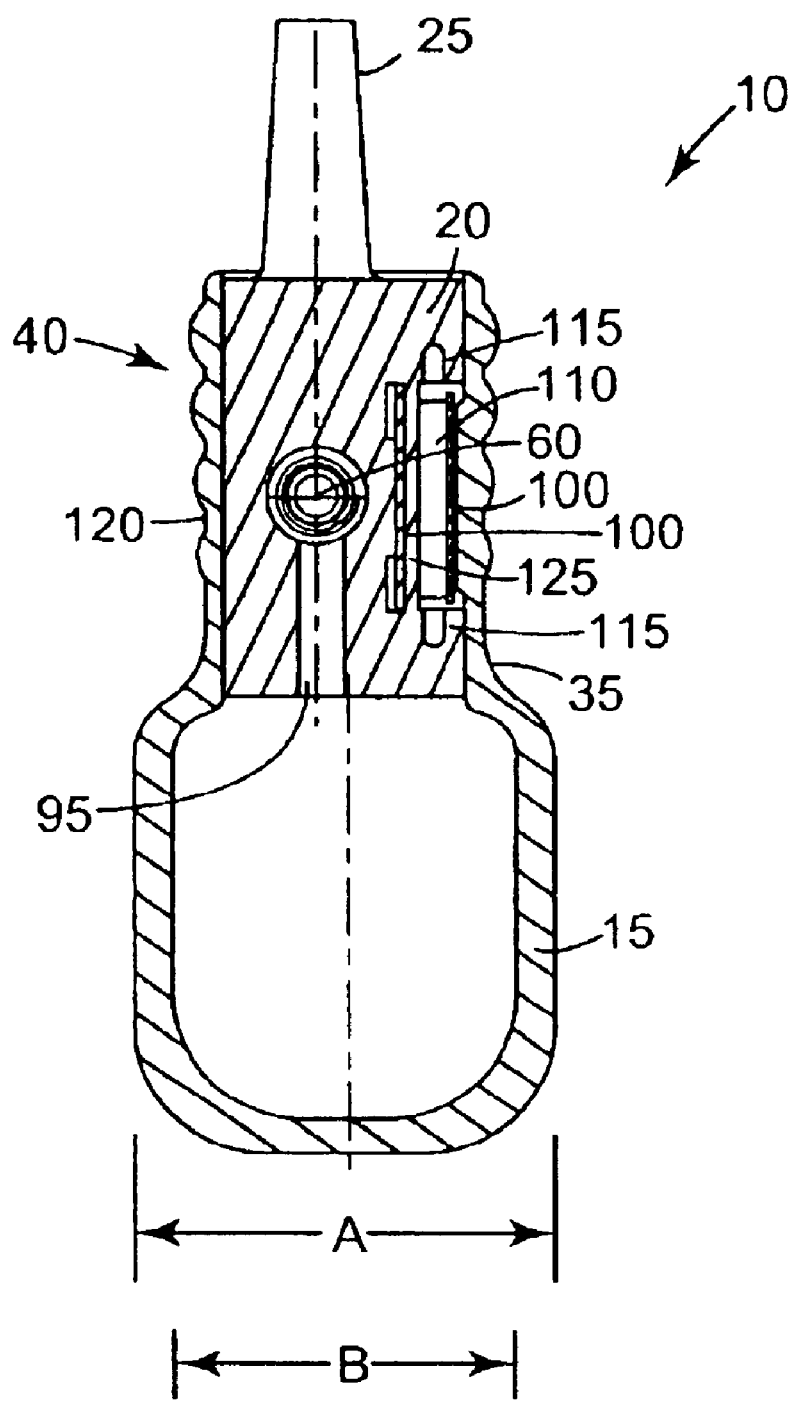
FIG. 6 is a side sectional view of the pump and valve assembly illustrated in FIG. 1.

FIG. 6 illustrates a side sectional view of pump and valve assembly 10. Actuating bar 100 only extends along a portion of valve block 20. When a patient engages first major panel 120, actuating bar 100 will be relatively small in comparison to the surface area defined by the patient's finger. To further facilitate the ease with which the patient can compress actuating bar 100 and effectively unseat reservoir poppet 65, valve block 20 is enhanced by valve block tabs 115, which help define valve block recess 110 within which actuating bar 100 is seated. Thus, when the patient engages first major panel 35, moving it towards second major panel 120, this movement is enhanced by the flexibility of valve block tabs 115 allowing a larger portion of first major panel 35 to deflect into valve block recess 110.

The ease with which the patient can identify, grasp and compress the relevant portion of pump and valve assembly 10, may ultimately determine the patient's overall satisfaction with the device. FIG. 6 illustrates yet another factor which serves to facilitate this. The width of pump bulb 15 is defined as A, while the width of valve housing 12 is defined as B. Notably, the width A of valve housing 12 is smaller than the width A of pump bulb 15. The relevant factor is that pump bulb 15 is sized differently than valve housing 12. It does not matter which component is larger or smaller.

Thus, when the patient grasps pump and valve assembly 10, there are several factors that can be utilized to determine which portion the patient is grasping. First, the orientation of pump bulb 15 towards the bottom is an initial indicator. The textured surface 40 of the major panels 35 and 120 is a secondary indicator and the relative size difference between pump bulb 15 and valve housing 12 is a tertiary indicator. These components also work together along with actuating bar 100 to make it easier for the patient to compress valve housing 12 and open the internal poppets, allowing the cylinders to be deflated. This is accomplished because major panels 35 and 120 are larger and easier to grasp and their compression towards one another actuates actuating bar 100 which in turn actuates and opens reservoir poppet 65. The textured surface 40 makes it easier for the patient to grip valve housing 12 during this process. Finally, the configuration of actuating bar 100 can be configured to provide positive feedback to the patient that they are successfully opening the valves to allow for deflation. That is, actuating bar 100 can be provided with a bent area configured such that when actuating bar 100 is actuated, it will cause a clicking sensation that is audibly or physically sensed by the patient to let them know that they have sufficiently compressed valve housing 12. Other identifying devices or configurations could be used as well.

Figure 7:
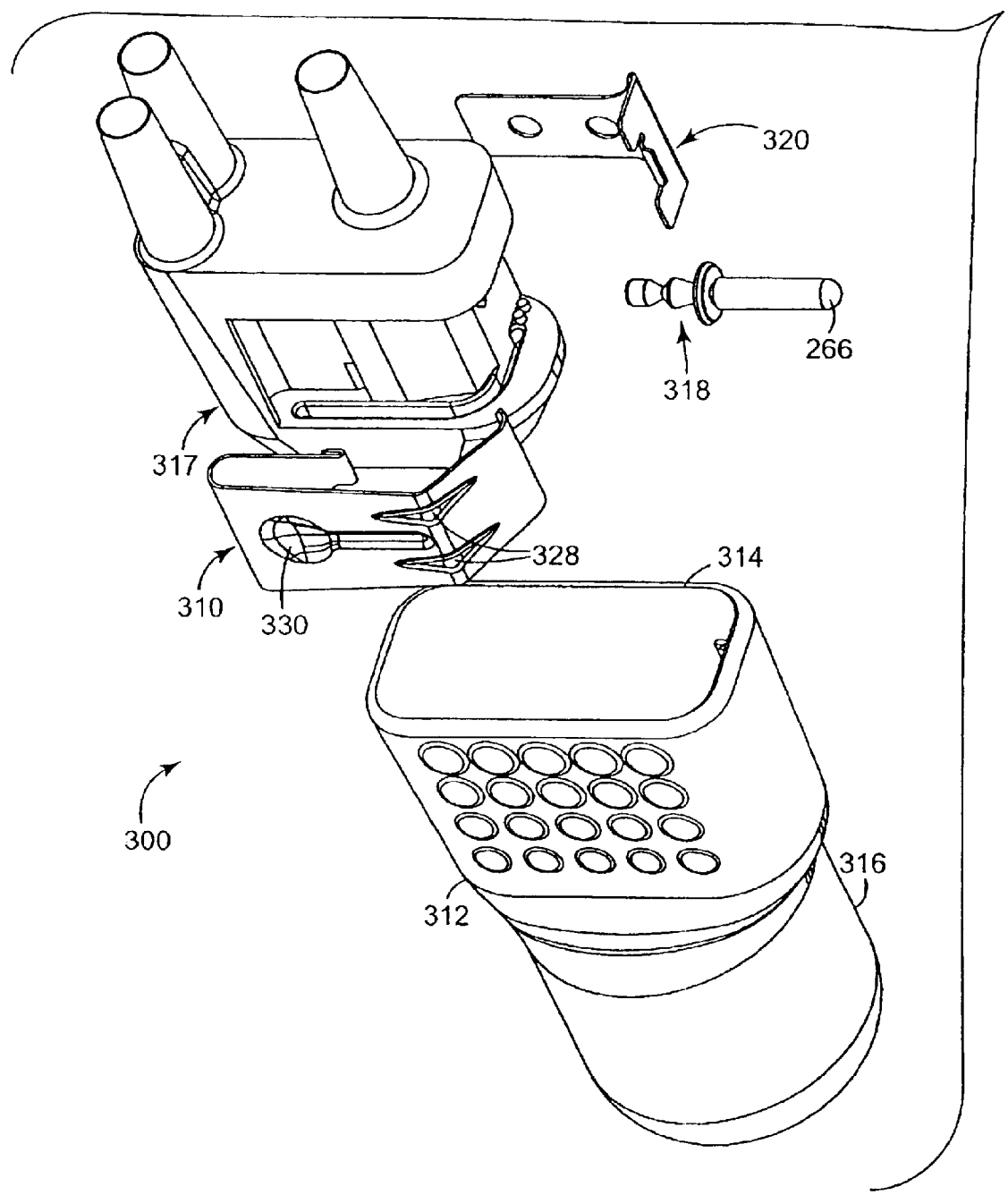
FIG. 7 is an exploded perspective view of an alternative embodiment of the present invention.

FIGS. 7–12 illustrate an alternative embodiment of pump and valve assembly 300 in which certain modifications have been made to further improve performance. FIG. 7 shows an exploded view of the alternative pump and valve assembly 300 with an improved actuating bar 310, a pump bulb 316, an improved check valve 318, and a poppet support 320. Assembly 300 comprises a valve block 317 for housing fluid passageways that inter-connect inflatable cylinders and a reservoir (not shown), as discussed in the embodiments above. Actuating bar 310, having a plurality of ribs 328 and 330, attaches to a side of valve block 317 and is positioned to engage an end of a reservoir poppet 318. Reservoir poppet 318 is a check valve that operates to control fluid flow into and out of the reservoir, and is to be positioned within the passageway of valve block 317. Poppet support 320 is to be disposed on an end of valve block 317, proximate an end 266 of the reservoir poppet 318, to prevent sideways sliding of the reservoir poppet 318 during actuation of the pump. The pump bulb 316 is to be located over valve block 317, actuating bar 310, reservoir poppet 318, and poppet support 320. As discussed in the embodiments above, pump bulb 316 comprises major panels 312 and 314 with textured surfaces that allow patients to easily identify that portion of valve assembly 300. When a patient applies pressure to major panels 312 and 314, major panel 312 engages actuating bar 310. Reservoir poppet 318, actuating bar 310 and poppet support 320 are described in detail below.

Figure 8B:
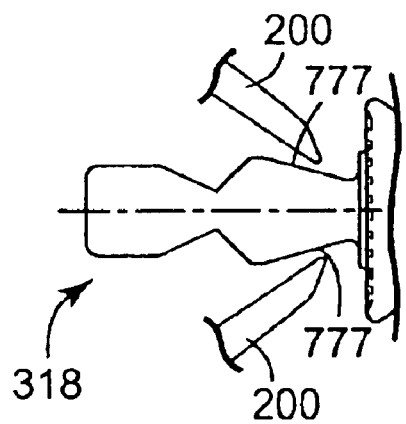
FIGS. 8B and 8C are more detailed illustrations of portions of the reservoir poppet, with FIG. 8B showing a poppet taper and FIG. 8C showing a previous design.
Figure 8A:
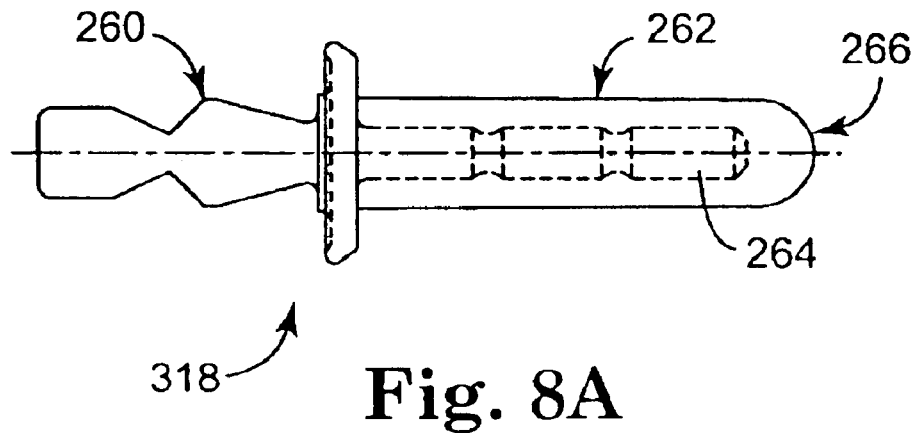
FIG. 8A is a side view of the reservoir poppet with a plastic portion of the embodiment of FIG. 7.

As illustrated in FIG. 8A, reservoir poppet 318 comprises an elongate rigid member 260 and a synthetic member 262. Synthetic member 262 is disposed over a segment/post portion 264 of rigid member 260. Rigid member 260 is preferably made of a metal material, such as steel, stainless steel, or the like. Synthetic member 262 is preferably made of a strong, durable plastic material, for example acetal, nylon and/or polyester, to prevent undesired frictional contact with actuating bar 310. Synthetic member 262 is rigidly attached to rigid member 260 by molding, bonding, or the like. Synthetic member 262 prevents premature wearing of reservoir poppet 318 and actuating bar 310. For example, synthetic member 262 prevents direct metal-on-metal contact between metal reservoir poppet 318 and actuating bar 310. The addition of the synthetic member 262 reduces the frictional interaction of reservoir poppet 318 and actuation bar 310 that typically occurs at the end 266 of reservoir poppet 318. Thus, the risk of marking or deforming reservoir poppet 318 and actuation bar 310 is reduced, and the useful life of the two components is extended.

Figure 8C:
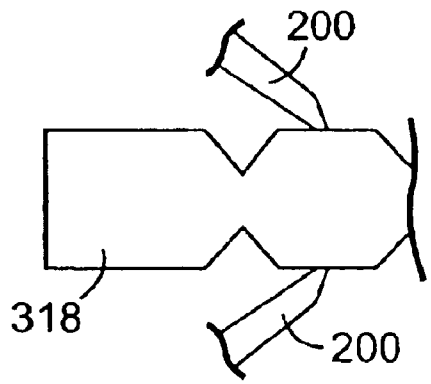

As shown in FIG. 8B, a poppet taper 777 provides a very useful novel feature. When poppet 318 is pushed back into the release or deflation mode, taper 777 permits the lip seal 200 to separate from poppet 318. This allows fluid from the cylinder to pass unimpeded through the pump. Without taper 777, lip seal 200 would rest on poppet 318 as shown in FIG. 8C. The arrangement of FIG. 8C requires pressure to open lip seal 200 before fluid is allowed to pass from the cylinder to the reservoir. Moreover, when the pressure drops below a minimum value, lip seal 200 closes on reservoir poppet 318 and traps pressurized fluid in the cylinder. This typically happens at a less than flaccid cylinder condition. Unfortunately, to force this pressurized fluid out of the cylinder when it is at this state, the patient must squeeze his penis and the cylinder to increase cylinder pressure and open the lip seal design.

Figure 9:
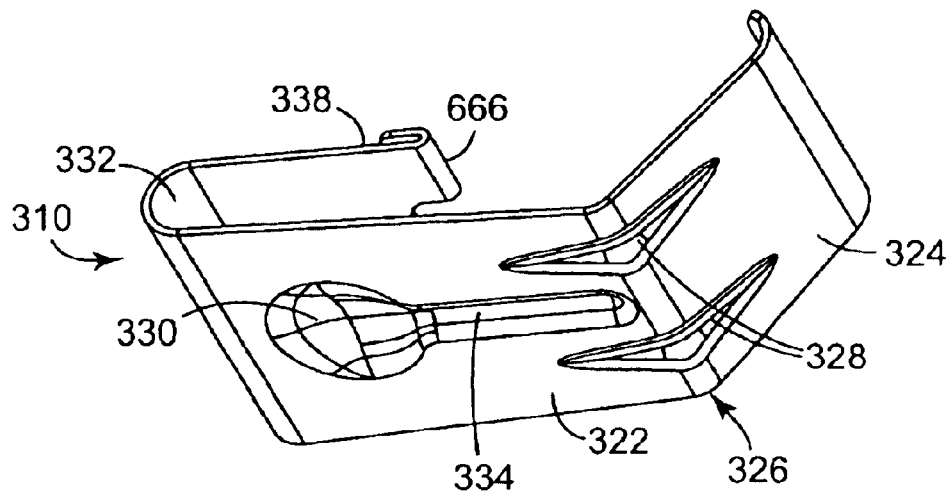
FIG. 9 is perspective view of the actuating bar of the embodiment of FIG. 7.
Figure 10A:
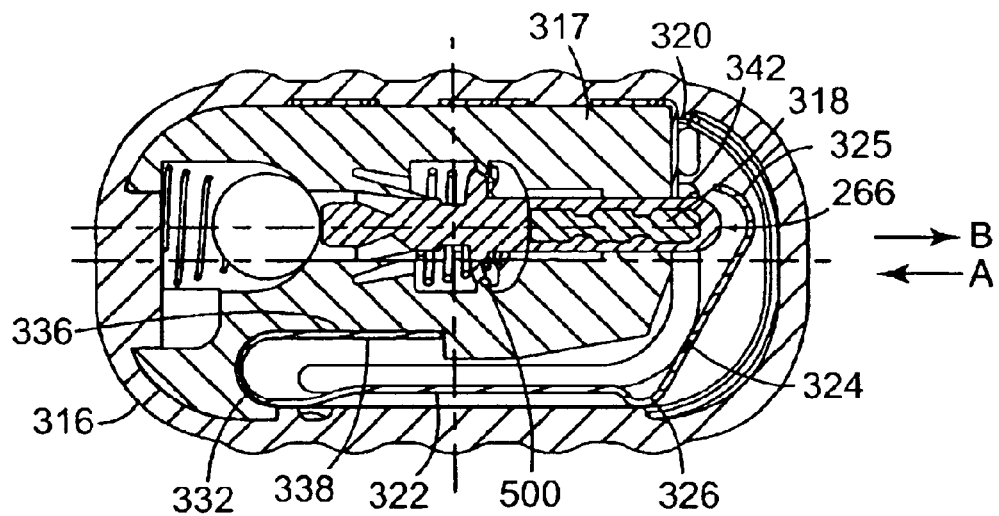
FIG. 10A is a top sectional view of the embodiment of FIG. 7.

As illustrated in FIGS. 7, 9 and 10A–C, actuating bar 310 is a thin elongated member formed to comprise an actuating face 322 and an actuating arm 324 that are connected by an angle portion 326. A U-shaped portion 332 connects a connecting end 338 to actuating face 322. As shown in FIG. 10A, actuating bar 310 is disposed within valve block 317 by securement of end 338 into a valve block interface 336.

Connecting end 338 includes two forked portions 666, one of which is shown in FIG. 9. As shown in FIG. 10A, actuating bar 310 is disposed within valve block 317 by securement of end 338 into a valve block interface 336. The forked portions 666 of connecting end 338 help hold actuating bar 310 in place.

Angle portion 326 provides actuating bar 310 with a spring force that is applied to an end of reservoir poppet 318 in the same manner as described in the embodiments of above. Angle portion 326 permits actuating face 322 of actuating bar 310 to extend along a side of the length of valve block 317, while actuating arm 324 extends along a side of the width of valve block 317. The configuration of actuating bar 310 enables it to engage an end 266, e.g., the tip, of reservoir poppet 318. Actuating arm 324 includes, opposite angle portion 326, a curved portion 325 for complementary engagement with reservoir poppet end 266. See FIG. 10C. Preferably, curved portion 325 presents a smooth face to the side of the pump shell when the pump shell acts on the curved portion 325 of the actuating bar 310.

Figure 10B:
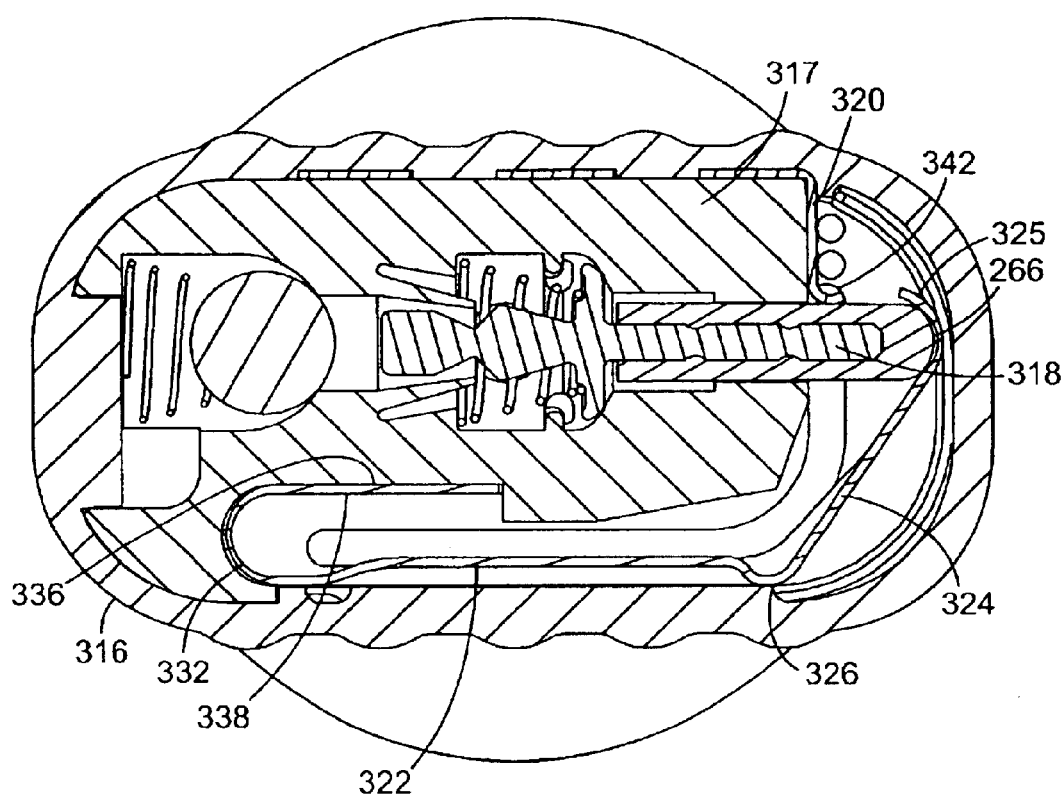
FIG. 10B is a sectional view of the embodiment of FIG. 7 showing the elements when the cylinders are inflated.
Figure 10C:
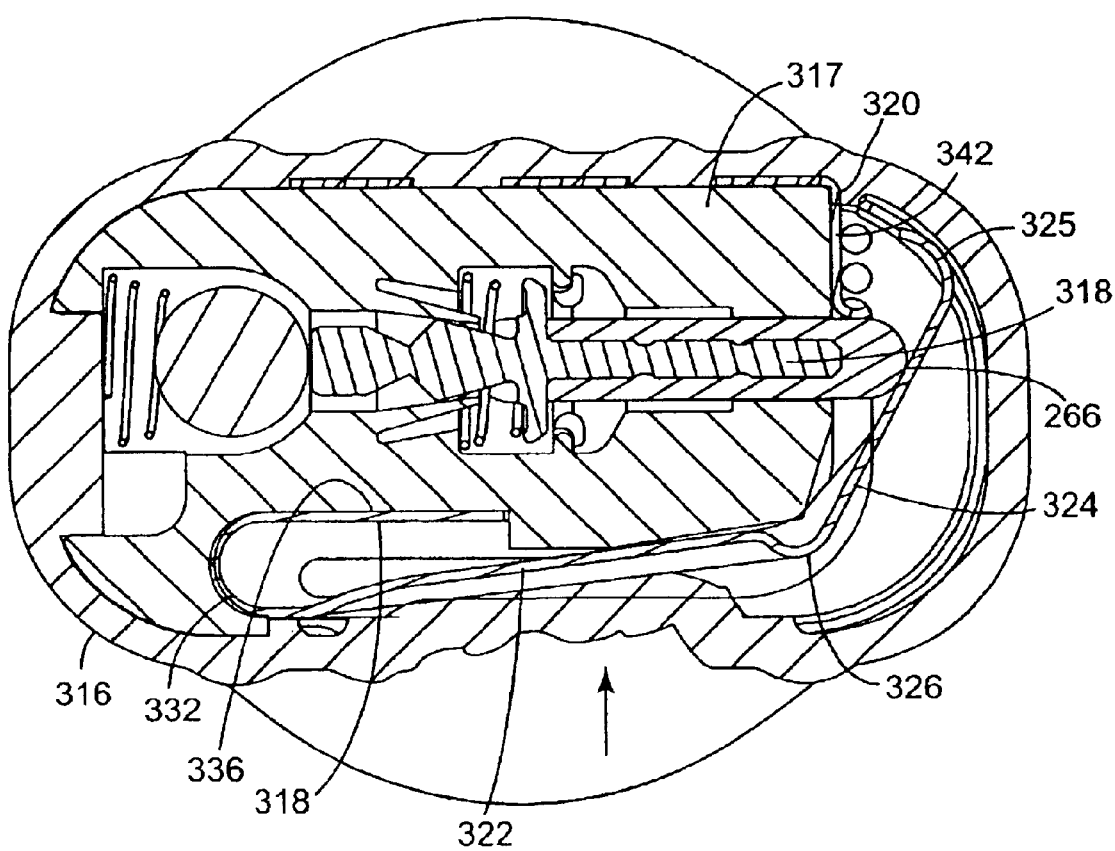
FIG. 10C is a sectional view of the embodiment of FIG. 7 showing the elements actuated to afford flow of fluid from the cylinders to the reservoir.

As discussed in the embodiments above, when the patient grasps valve assembly 300 in virtually any orientation and applies pressure, actuating bar 310 acts either directly or indirectly to open the appropriate check valves (FIG. 10C). Thus, when the patient grasps a portion of the pump and valve assembly 300 other than pump bulb 316, compression will result in the flexing of actuating bar 310. During compression, actuating face 322 flexes inwardly and actuating arm 324 flexes toward reservoir poppet end 266, as indicated by arrow A in FIG. 10A. Actuating arm 324 moves into engagement with reservoir poppet end 266. The movement of actuating arm 324 forces axial movement of reservoir poppet 318 in the same direction as arrow A and into an open position. The axial movement of reservoir poppet 318 permits fluid to flow through the fluid pathways to the reservoir and allows the cylinders to deflate.

When the patient ceases compression of the valve assembly 300, actuating face 322 returns to its original position. Actuating arm 324 moves in a direction indicated by arrow B in FIG. 10A, and out of forceful engagement with end 266 (see FIG. 10B). This movement permits reservoir poppet 318 to return to the position shown in FIG. 10A.

As disclosed in the embodiments above, angle portion 326 in actuating bar 310, and its resistance to flexing outwardly, creates a desirable stiffness, bias or spring force. Actuating bar 310 is capable of forcing reservoir poppet 318 into a position (see FIG. 10C) that permits the flow of fluid through the fluid pathways and back into the reservoir. For example, during patient compression of pump and valve assembly 300, curved portion 325 of actuating arm 324 enters engagement with end 266. Actuating arm 324 applies the spring force to poppet end 266 to force reservoir poppet 318 into the interior of valve block 317 and into an open/active position. When actuating arm 324 is engaged with poppet end 266, there is an opposing force created by the resistance of reservoir poppet 318 to move into the open position. This opposing force may overcome the spring force and cause actuating arm 324 to improperly deflect. Stated alternatively, this improper deflection occurs when the opposing force exerted against actuating bar 310 overcomes the inherent spring force and causes actuating arm 324 to bend backwards or buckle.

To prevent improper deflection, stiffening ribs 328 are formed on actuating bar 310, as shown by FIG. 9. Each rib 328 is a recess or impression formed in actuating bar 310 and extends across angle portion 326. Ribs 328 increase the strength and stiffness of angle portion 326, which increases the resistance to deflection during actuation. The surface area of angle portion 326 is disposed along a given plane. Ribs 328 divide the surface area of angle 326 with recesses that extend into another plane. The portions of material extending in a different plane increase the stiffness of angle 326. This increase in stiffness decreases the likelihood of improper deflection of actuating arm 324. The absence of improper deflection thus ensures full axial travel of reservoir poppet 318 and attainment of the open position. Additionally, increasing the strength of angle 326 prevents any permanent deformation that might occur due to repeated actuation. This resistance to deflection or bending helps prevent fatigue of actuating bar 310 and extends the useful life of the component. Although ribs 328 may be formed by a curved recess that extends in a plane perpendicular to the surface of angle 326 as shown in the Figures, ribs 328 may exist in many different orientations. A sufficient number of ribs 328 may be provided to angle 326 so as to achieve a predetermined deflection resistance. For example, two ribs 328 are provided in angle 326, as shown in FIG. 9.

As discussed above, when a patient compresses valve assembly 300 to deflate the prosthesis, actuating face 322 flexes or pivots inwardly about U-shaped portion 332. This causes actuating face 324 to move into engagement with poppet end 266 (FIG. 10B). The repeated application of force to a particular area of actuation face 322, may cause permanent deformation. As shown in FIG. 9, a recess formed in and disposed along actuating face 322 defines a rib 330. Rib 330 strengthens and stiffens actuating face 322 to limit deformation. Rib 330 extends into a plane other than the plane created by the surface of actuating face 322 to increase its resistance to bending. During patient compression, rib 330 distributes the force applied throughout actuating face 322 rather than permit the compression force to be concentrated in one area. Thus, actuating face 322 properly flexes while resisting permanent deformation. Rib 330 may be shaped to distribute the compression force in any desired pattern. For example, as shown in FIG. 9, rib 330 may be a spoon-shaped impression centrally formed on actuating face 322 with a larger oval portion disposed toward U-portion 332 of actuating bar 310. An elongate portion 334 of spoon-shaped rib 330 extends toward angle 326. This shape is preferred since the compression forces applied to flex actuating face 322 are evenly distributed over its entire surface.

The relatively thin composition of actuating bar 310 is beneficial for several reasons. During actuation, U-portion 332 bends to flex actuating face 322 inwardly and actuating face 322 moves actuating arm 324 into engagement with reservoir poppet 318. After actuation, U-portion 332, actuating face 322 and actuating arm 324 return to their original position. With an actuating bar formed with a thick material, U-portion 332 does not properly bend during actuation. In operation with a thick actuating bar 310, U-portion 332 does not bend, and connecting end 338 is pushed into valve block 317 causing its inner cavities to distort, such that annular ring 500 (FIG. 10A) of valve block 317 becomes out-of-round and impedes or stops the movement of poppet 318 in direction A. Preferably, actuating bar 310 is a thin member made of a material with sufficient thickness and stiffness to provide the necessary spring force to avoid improper deflection. For example, actuation bar 310 may be formed from a stainless steel sheet having a thickness of approximately 0.0100 inches. Actuation bar 310 may be made of various metal materials, plastic, or the like.

Figure 11:
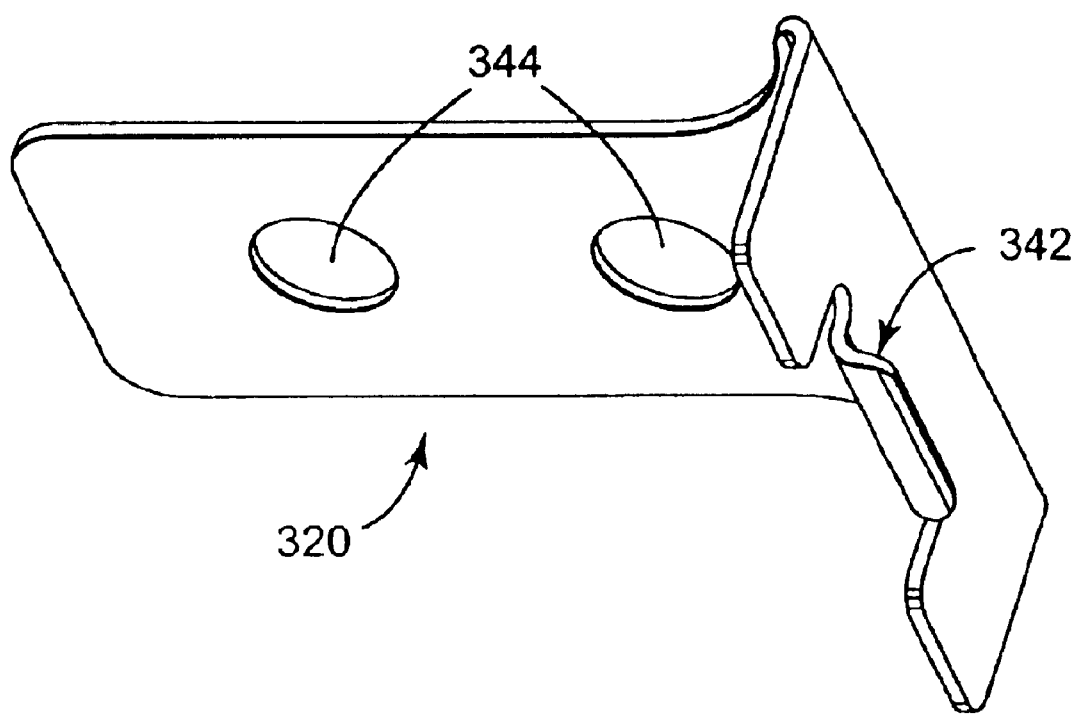
FIG. 11 is a perspective view of the poppet support of the embodiment of FIG. 7.
Figure 12:
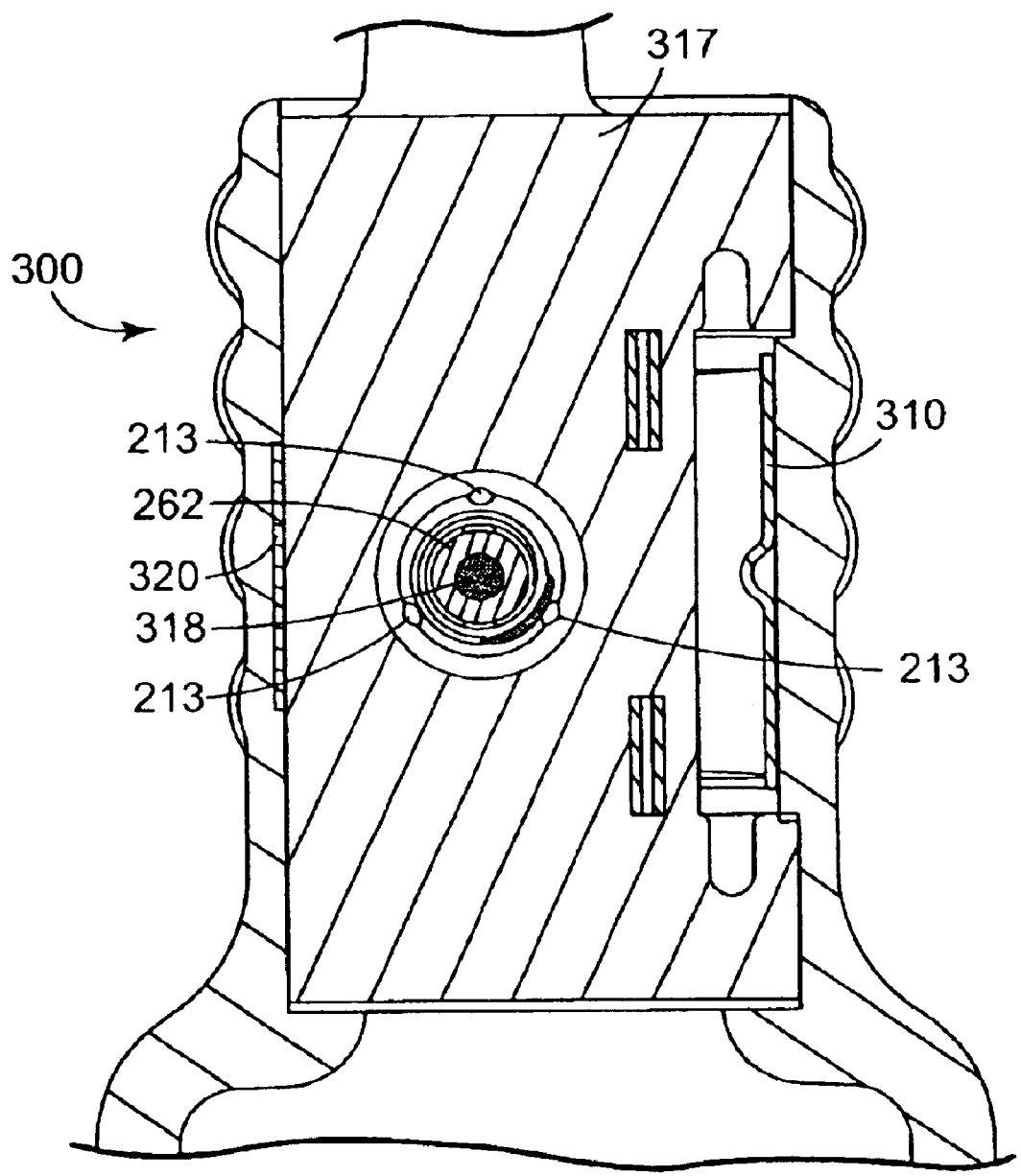
FIG. 12 is a sectional view of the embodiment of FIG. 7.

Since the engagement of actuating arm 324 to poppet end 266 is applied from essentially one side of reservoir poppet 318, the applied spring force is not completely along a longitudinal axis of reservoir poppet 318. The spring force is applied to poppet end 266 in both the axial and transverse/sideways directions. The sideways force has the unintended consequence of tipping reservoir poppet 318 sideways into valve block 317. In response, valve block 317 deforms to cause reservoir poppet 318 to be misaligned. This misalignment results in reservoir poppet 318 being restrained from moving axially into valve block 317 to reach an activated/open position. As shown in FIGS. 10–11, a stiff poppet support 320 is provided to prevent the misalignment of reservoir poppet 318.

As shown in FIG. 11, poppet support 320 is an elongate, generally L-shaped member comprising a shelf 342 at one end. Apertures 344 are provided in a portion of support 320 to attach poppet support 320 to valve block 317. See FIG. 10A. Poppet support 320 wraps around a portion of valve block 317 and rests against a portion of poppet end 266. Shelf 342 provides a smooth surface for a segment of reservoir poppet 318 to slide axially along during reservoir poppet 318 travel between open and closed positions. During actuation, curved portion 325 of actuating bar 310 applies a spring force to move reservoir poppet 318 to an open position. Poppet support 342 prevents sideways movement of reservoir poppet 318 as the poppet is forced into the interior of valve body 317. Poppet support 320 ensures the proper alignment of reservoir poppet 318 to easily move axially into valve body 317 to the open position.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. A method of using an inflatable implanted prosthesis comprising:

implanting an inflatable prosthesis into a patient, said prosthesis including a pump assembly including a periphery with opposing surfaces;

inflating said prosthesis with a pump included in said pump assembly;

randomly selecting any opposing surfaces on the periphery of said pump assembly; and compressing said randomly selected opposing surfaces of said pump assembly to deflate said prosthesis.

2. A method as set forth in claim 1, wherein compressing includes moving a check valve internal to said pump into a position to allow said prosthesis to become deflated.

3. A method as set forth in claim 2, wherein said pump assembly includes a check valve, said step of implanting an inflatable prosthesis into a patient comprises the step of implanting the prosthesis in a location affording patient palpation of the pump assembly, and the step of compressing includes the step of indirectly contacting said check valve through patient tissue.

4. A method as set forth in claim 3, wherein the opposing surfaces of the pump assembly include two opposing surfaces that extend along a length of the pump assembly, and the step of compressing includes the step of compressing the two opposing surfaces that extend along the length of said pump assembly.

5. A method as set forth in claim 3, wherein the opposing surfaces of the pump assembly include two opposing surfaces that extend along a width of the pump assembly, and the step of compressing includes the step of compressing the two opposing surfaces that extend along the width of said pump assembly.

6. A method as set forth in claim 1, wherein said pump assembly has a length and a deflation actuator positioned within said pump assembly, said deflation actuator extending along the length of said pump assembly, and
wherein the step of compressing includes the step of compressing the deflation actuator.

7. A method as set forth in claim 6, wherein said deflation actuator includes a valve actuation bar.

8. A method of using an inflatable prosthesis comprising:
implanting an inflatable prosthesis into a patient,
said prosthesis including a pump, a reservoir, and a pump assembly having a periphery, a bar and a check valve capable of being placed in a seated position;
inflating said prosthesis with the pump;
when deflation is desired, randomly selecting surfaces on the periphery of said pump assembly; and
physically compressing said randomly selected surfaces of said pump assembly to deflate said prosthesis, wherein compressing the surfaces activates the bar which permits the check valve to move from the seated position, permitting a flow of fluid into the reservoir.

9. A method as set forth in claim 8 wherein the step of compressing includes the step of preventing the sideways movement of the check valve.

10. A method as set forth in claims 9, wherein said step of implanting an inflatable prosthesis into a patient comprises the step of implanting the prosthesis in a location affording patient palpation of the pump assembly, and
said step of physically compressing includes the step of indirectly contacting said valve through patient tissue.

11. A method as set forth in claim 9, wherein the step of compressing includes the step of compressing two opposing surfaces that extend along a length of said pump assembly.

* * * * *